United States Patent [19]

Kimura et al.

[11] Patent Number: 4,857,515
[45] Date of Patent: Aug. 15, 1989

[54] CERTAIN ANTIHYPERTENSIVE 1,4-DIHYDRO-6-METHYL-5-PHOSPHONIC ACID-4-ARYL-3-CARBOXYLIC ACID-2-CYANO DIESTERS

[75] Inventors: Kiyoshi Kimura, Takatsuki; Masahiro Kise, Kyoto; Iwao Morita, Tsuzuki; Toshio Tomita, Kusatsu; Masami Tsuda, Joyo, all of Japan

[73] Assignee: Nippon Shinyaku Co., Ltd., Japan

[21] Appl. No.: 115,170

[22] Filed: Oct. 30, 1987

[30] Foreign Application Priority Data

Oct. 31, 1986 [JP] Japan .................................. 61261587

[51] Int. Cl.$^4$ ...................... C07F 9/58; A61K 31/44; A61K 31/665
[52] U.S. Cl. ......................................... 514/89; 546/21
[58] Field of Search ............................. 546/21; 514/89

[56] References Cited

U.S. PATENT DOCUMENTS 4,535,073  8/1985  Kimura et al. ...................... 514/89
4,576,934  3/1986  Seto et al. ............................ 514/85

Primary Examiner—Alan L. Rotman
Attorney, Agent, or Firm—Jacobs & Jacobs

[57] ABSTRACT

A compound of formula (I):

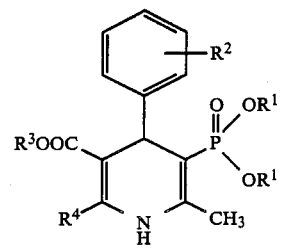

wherein $R^1$ is alkenyl or alkyl or both of the depicted $R^1$ groups together represent trimethylene and form a six-membered ring together with the depicted oxygen and phosphorus atoms, $R^2$ is nitro, trifluoromethyl or halogen, $R^3$ is alkyl, and $R^4$ is dimethoxymethyl, formyl, hydroxymethyl or nitrile.

10 Claims, No Drawings

CERTAIN ANTIHYPERTENSIVE 1,4-DIHYDRO-6-METHYL-5-PHOSPHONIC ACID-4-ARYL-3-CARBOXYLIC ACID-2-CYANO DIESTERS

The present invention relates to 2-substituted, 1,4-dihydropyridine derivatives of the formula (I) below,

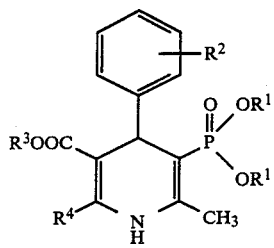
(I)

wherein $R^1$ is alkenyl or alkyl or both of the depicted $R^1$ groups together represent trimethylene and form a six-membered ring together with the depicted oxygen and phosphorus atoms; $R^2$ is nitro, trifluoromethyl or halogen; $R^3$ is alkyl; and $R^4$ is dimethoxymethyl, formyl, hydroxymethyl or nitrile.

Compounds (I) of the invention are calcium antagonists and have hypotensive and blood vessel dilating activity. As such, they are useful in the prophylaxis and treatment of circulatory diseases, such as hypertension, angina pectoris and cerebral circulation disorders.

It is known that some 1,4-dihydropyridine derivatives have coronary vasodilating and hypotensive activity. For example, compounds of formula (X) are known:

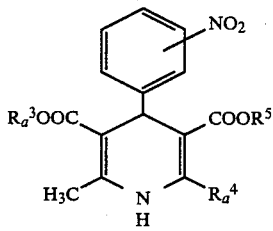
(X)

wherein $R_a^4$ is hydroxymethyl or nitrile. See, e.g. Japanese laid open applications Nos. 54/160384, 55/62065, 55/153768, 55/40678, 57/175164, 59/231017 and Japanese examined applications Nos. 48827/84 and 48828/84).

As can be seen, the known compounds of formula (X) are structurally remote from the compounds of formula (I) of the present invention.

Examples of preferred alkenyl for $R^1$ in formula (I) include straight or branched chain alkenyl of from about 2 to about 6 carbon atoms, such as, for example, vinyl, allyl, isopropenyl, 2-methallyl, 2-butenyl and 3-butenyl.

Examples of preferred alkyl for $R^1$ include straight or branched chain alkyl of from about 1 to about 6, most preferably from about 1 to about 4, carbon atoms such as, for example, methyl, ethyl, n-propyl, isopropyl, n-butyl, isobutyl, tert-butyl, etc.

Examples of preferred halogen represented by $R^2$ include chlorine, bromine, fluorine and iodine. It is preferred that the nitro, trifluoromethyl or halogen represented by $R^2$ is substituted at the 2- or 3-position of the depicted phenyl ring.

Examples of preferred alkyl represented by $R^3$ include straight or branched alkyl of from about 1 to about 6, most preferably from about 1 to about 4, carbon atoms, such as, for example, methyl, ethyl, n-propyl, isopropyl, n-butyl, isobutyl, tert-butyl, etc.

The compounds (I) of the present invention have asymmetric carbon atoms and all optically active compounds and mixtures thereof are included within the present invention.

All of the compounds (I) of the present invention may be manufactured, for example, by the following routes:

First Step:

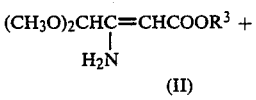

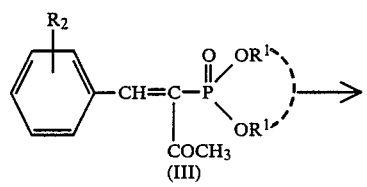

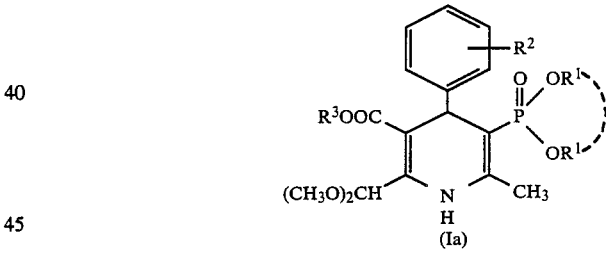

($R^1$, $R^2$ and $R^3$ are the same as described above)

Second Step:

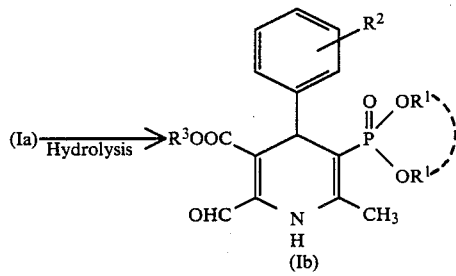

($R^1$, $R^2$ and $R^3$ are the same as described above)

Third Step:

-continued

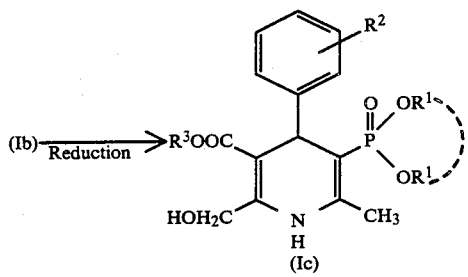

($R^1$, $R^2$ and $R^3$ are the same as described above)

Fourth Step:

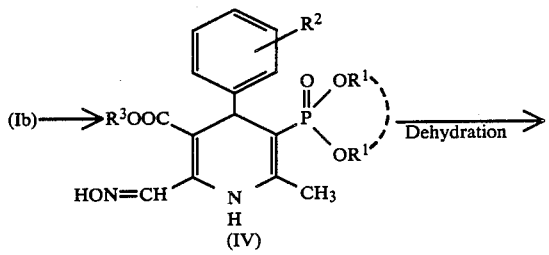

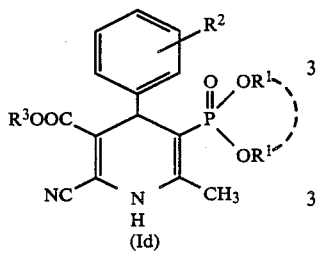

($R^1$, $R^2$ and $R^3$ are the same as described above)

It will be recognized that each of compounds (Ia), (Ib), (Ic) and (Id) is within the scope of formula (I) above.

Each step will be further illustrated as follows:

First Step.

A benzylidene compound (III) is reacted with an aminocrotonate compound (II) to give compound (Ia). This reaction is usually conducted in the presence or absence of a solvent which is inert in the reaction, such as alcohols (e.g. methanol and ethanol), aromatic hydrocarbons (e.g. benzene, toluene and xylene), halogenated hydrocarbons (e.g. chloroform and methylene chloride), acetonitrile, N,N-dimethylformamide, water and mixtures thereof, at room temperature or with heating (conveniently at the boiling point of the solvent used). The amount of (II) is usually about 1 to about 1.5 moles per mole of (III).

Second Step.

(Ia) is hydrolyzed to give a formyl compound (Ib). This hydrolysis may be conducted by a method known per se. Thus, usually, the reaction is carried out in a solvent which is inert in the reaction, such as ketones (e.g. acetone and methyl ethyl ketone), alcohols (e.g. methanol and ethanol), ethers (e.g. dioxane), N,N-dmethylformamide, N-methylmorpholine, dimethyl sulfoxide, water or a mixture thereof under acidic conditions (i.e. in the presence of an inorganic acid, such as hydrochloric acid or sulfuric acid or an organic acid, such as formic acid, acetic acid, trifluoroacetic acid or p-tol- uenesulfonic acid) with cooling or warming (preferably within the range of 0° to 10° C.). The amount of the acid used is usually in a catalytic amount or around two moles per mole of (Ia).

Third Step.

The formyl compound (Ib) is reduced to give the hydroxymethyl compound (Ic). This reduction may be conducted by a method known per se. Thus, a reducing agent (e.g. alkali borohydrate, such as sodium borohydrate, potassium borohydrate and lithium borohydrate) is used in a solvent which is inert in the reaction (e.g. alcohols such as methanol and ethanol; N,N-dimethylformamide; water or a mixture thereof) or a catalytic reduction may be used. In the catalytic reduction, catalysts usually used for such reaction (e.g. palladium carbon, palladium chloride, rhodium carbon, etc.) may be used. There is no particular limitation as to the reaction temperature but, usually, the reaction is conducted with cooling or warming or, preferably, in the range of −10° to 0° C.

Fourth Step.

The formyl compound (Ib) is made to react with hydroxylamine or a salt thereof (e.g. a salt with an inorganic acid, such as hydrochloric acid or sulfuric acid, or a salt with an organic acid, such as acetic acid or p-toluenesulfonic acid) to give the oxime (IV), which is reacted with a dehydrating agent to give (Id). The first half of the reaction may be conducted by a method known per se. Thus, the reaction is usually carried out in an inert solvent (e.g. alcohols, such as methanol and ethanol; ethers such as dioxane; N,N-dimethylformamide; water; or a mixture thereof) in the presence of an acid catalyst (e.g., an inorganic acid, such as hydrochloric acid, hydrobromic acid, sulfuric acid, etc.; an organic acid, such as formic acid, acetic acid, p-toluenesulfonic acid, etc.; or a Lewis acid such as boron trifluoride, silicone tetrachloride, titanium tetrachloride, etc.) or, under basic conditions using free hydroxylamine, in the presence of the above hydroxylamine salt and base (inorganic or organic base, such as sodium acetate, potassium carbonate, pyridine, triethylamine, etc.). There is no particular limitation on the reaction temperature, but, usually the reaction is conducted with cooling or warming. The amount of hydroxylamine used is about 1 to about 1.5 moles per mole of (Ib).

The latter half of the reaction may also be carried out by a method known per se. Thus, the reaction may be conducted in an inert solvent (e.g. halogenated hydrocarbons, such as methylene chloride, chloroform, etc.; ethers, such as dimethyl ether, tetrahydrofuran, dioxane, etc.; N,N-dimethylformamide; pyridine; acetic acid; formic acid; etc.) using a dehydrating agent. Examples of the dehydrating agents include inorganic acids, such as sulfuric acid, phosphoric acid, polyphosphoric acid, etc., organic acids, such as formic acid, acetic acid, ethanesulfonic acid, p-toluenesulfonic acid, etc., acid anhydrides, such as acetic anhydride, phthalic anhydride, etc., acid halides such as acetyl chloride, benzoyl chloride, ethyl chlorocarbonate, etc., carbodiimides such as N,N'-dicyclohexylcarbodiimide, N-cyclohexyl-N'-morpholinoethylcarbodiimide, etc., or a dehydrating agent which can convert hydroxyliminomethyl to cyano, such as N,N'-carbonyldiimidazole. The reaction is usually carried out at ambient temperature or with heating. The amount of the dehydrating agent is usually about 1 to about 4.0 moles per mole of (IV).

The resulting desired compound (I) may be isolated and purified by conventional separating and purifying means, such as, for example, extraction, concentration, neutralization, filtration, recrystallization, column chromatography, thin layer chromatography, etc.

Starting materials (II) and (III) of the present invention are known and may be manufactured by known methods, such as disclosed in Japanese examined application No. 48828/84 and Japanese laid open applications Nos. 59/161392 and 60/248693.

As shown in the Test Example which follows, the compounds (I) of the present invention are calcium antagonists and have hypotensive and blood vessel dilating activity. As such, they are useful in the prophylaxis and treatment of circulatory diseases, such as hypertension, angina pectoris and cerebral circulation disorders.

Compounds (I) of the invention are used for the prophylaxis and treatment of hypertension, angina pectoris or cerebral circulation disorders in animals, including humans, by administering to the sufferer a therapeutically effective amount of the compound (I) of the invention, preferably in the form of a pharmaceutical composition comprising a therapeutically effective amount of compound (I) in combination with a pharmaceutically acceptable, nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, third or fourth of a single dose. A single dose preferably contains an amount sufficient to produce the desired therapeutic effect by administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dosage of compound (I) for use in the prophylaxis or treatment of hypertension, angina pectoris or cerebral circulation disorders in humans will be from about 1 to about 1000 mg., preferably from about 2 to about 100 mg. In some instances, a sufficient therapeutic effect can be obtained at a lower dose, while in others a larger dose will be required.

While the routes of administration of the compounds (I) of the invention include oral, parenteral (i.e., intramuscular, intraperitoneal and intravenous), topical and rectal, oral administration is particularly preferred.

The preferred pharmaceutical compositions are therefore those in a form suitable for oral administration, such as tablets and liquids.

The present invention is further illustrated by way of working examples and test example showing the manufacture and utility of the present invention compounds, respectively.

EXAMPLE 1

Methyl 2-dimethoxymethyl-6-methyl-4-(2-nitrophenyl)-5-(2-oxo-1,3,2-dioxaphosphorinan-2-yl)-1,4-dihydropyridine-3-carboxylate Methyl 3-amino-4-dimethoxycrotonate (3.50 g) and 6.22 g of 2-[1-(2-nitrobenzylidene)acetonyl]-2-oxo-1,3,2-dioxaphosphorinane were dissolved in 30 ml of acetonitrile and heated to reflux for 30 hours. The reaction solution was concentrated in vacuo and the residue was purified by a flash chromatography to give 3.85 g of crude crystals which were recrystallized from ethyl acetate-ether. M.p. 174°–175.5° C.

Elem Anal for: $C_{20}H_{25}N_2O_9P$: Calculated C%=51.29; H%=5.38; N%=5.98. Found C%=51.14; H%=5.33; N%=5.93.

IR$\nu_{max}^{KBr}$max cm$^{-1}$; 3350, 3220, 3100, 1695, 1650, 1530, 1360, 1240, 1220, 1060.

NMR (CDCl$_3$) δ: 1.00~2.50 (2H,m), 2.45 (3H,d,J=2Hz), 3.29 (3H,s), 3.41 (3H,s), 3.58 (3H,s), 3.70~4.80 (4H,m), 5.61 (1H,d,J=11 Hz), 5.90 (1H,s), 6.70~7.00 (1H,m), 7.00~7.80 (4H,m).

EXAMPLE 2

Methyl 2-dimethoxymethyl-6-methyl-5-(2-oxo-1,3,2-dioxaphosphorinan-2-yl)-4-(2-trifluoromethylphenyl)-1,4-dihydropyridine-3-carboxylate Methyl 3-amino-4-dimethoxycrotonate (3.0 g) and 5.66 g of 2-[1-(2-trifluoromethylbenzylidene)acetonyl]-2-oxo-1,3,2-dioxaphosphorinane were heated to reflux for 70 hours in 80 ml of ethanol and the reaction solution was treated as same as in Example 1 to give oily 1,4-dihydropyridine compound.

NMR (CDCl$_3$) δ: 1.75 (2H,m), 2.40 (3H, d, J=2.5 Hz), 3.31 (3H,s), 3.35 (3H,s), 3.68 (3H,s), 3.70~4.71 (4H,m), 5.21 (1H, s), 5.83 (1H,s), 6.5~6.8 (1H,m), 7.10~7.51 (4H,m).

EXAMPLE 3

Methyl 5-diallyloxyphosphinyl-2-dimethoxymethyl-6-methyl-4-(3-nitrophenyl)-1,4-dihydropyridine-3-carboxylate Methyl 3-amino-4-dimethoxycrotonate (1.53 g) and 3.07 g of diallyl 1-(3-nitrobenzylidene)acetonylphosphonate were heated to reflux for 44 hours in 30 ml of ethanol and treated the same as in Example 1 to give 2.80 g of oily product.

IR $\nu_{max}^{film}$cm$^{-1}$: 1710, 1645, 1535, 1350, 1260, 1220, 1060.

EXAMPLE 4

Methyl 2-formyl-6-methyl-4-(2-nitrophenyl)-5-(2-oxo-1,3,2-dioxaphosphorinan-2-yl)-1,4-dihydropyridine-3-carboxylate Dimethylacetal (3.04 g) obtained in Example 1 was dissolved in 30 ml of acetone, 2 ml of 6N hydrochloric acid was dropped therein with ice cooling and stirring, and the mixture was kept at 5° C. in a refrigerator for 4 days. To the reaction solution was added 30 ml of ice water, the mixture was neutralized with sodium bicarbonate, concentrated in vacuo at room temperature, the residual solution was extracted with chloroform, the chloroform layer was washed with sodium chloride solution, evaporated to dryness, the residue was purified by subjecting to a flash column chromatography, and the 1.38 g of resulting crude crystals were recrystallized from etherethyl acetate to give yellow prisms. M.p. 135°–136° C.

Elem Anal for: $C_{18}H_{19}N_2O_8P$: Calculated: C%=51.19, H%=4.53, N%=6.63. Found: C%=51.32, H%=4.50, N%=6.68.

IR $\nu_{max}^{KBr}$cm$^{-1}$: 3360, 3300, 3080, 1940, 1695, 1530, 1370, 1230, 1050.

NMR (CDCl$_3$) δ: 1.70~1.78 (1H, m), 2.36~2.60 (1H, m), 2.55 (3H, d, J=2.0 Hz), 3.73 (3H, s), 3.85~4.08 (1H, m), 4.20~4.70 (3H, m), 5.75 (1H, d, J=10 Hz), 7.04~7.16 (1H, m), 7.26~7.56 (3H, m), 7.79 (1H, d, J=8 Hz), 10.34 (1H, s).

EXAMPLE 5

Methyl 2-formyl-6-methyl-5-(2-oxo-1,3,2-dioxaphosphorinan-2-yl)-4-(2-trifluoromethylphenyl)-1,4-dihydropyridine-3-carboxylate The dimethylacetal compound (1.43 g) obtained in Example 2 was dissolved in 6 ml of acetone, 1 ml of 6N hydrochloric acid was added thereto with ice cooling and stirring, the mixture was allowed to stand, stirred at ambient temperature for 1 hour, and purified by treating the same as that in Example 4 to give 1.06 g of oily product.

NMR (CDCl$_3$) δ: 1.40~1.82 (2H, m), 2.49 (3H, d, J=2.5 Hz), 3.75 (3H, s), 4.21~4.72 (4H, m), 5.44 (1H, d, J=10 Hz), 6.82~7.71 (5H, m), 10.23 (1H, s)

EXAMPLE 6

Methyl 5-diallyloxyphosphinyl-2-formyl-6-methyl-4-(3-nitrophenyl)-1,4-dihydropyridine-3-carboxylate The 2-dimethylacetal compound (2.79 g) obtained in Example 3 was dissolved in 30 ml of acetone, the solution was made to react and after-treated as same as in Example 4, and purified by a flash chromatography to give 1.34 g of oily 2-formyl compound.

IR $\nu_{max}^{film}$cm$^{-1}$: 1715, 1690, 1650, 1535, 1350, 1260, 1210, 1010.

EXAMPLE 7

Methyl 2-hydroxymethyl-6-methyl-4-(2-nitrophenyl)-5-(2-oxo-1,3,2-dioxaphosphorinan-2-yl)-1,4-dihydropyridine-3-carboxylate 2-Formyl compound (3.5 g) obtained in Example 4 was dissolved in 100 ml of methanol and 0.38 g of sodium borohydrate was added thereto with cooling at −10° C. and stirring. After one hour, the bath temperature was set at 0°–5° C. and the stirring was continued for 1 hour more. The reaction solution was neutralized with acetic acid with cooling and concentrated in vacuo at not higher than 30° C. The residue was extracted with chloroform, the extract was washed with water, dried and concentrated. The residue was subjected to a flash chromatography for purification to give 3.05 g of 2-hydroxymethyl compound which was recrystallized from ethyl acetate to give 2.53 g of pale yellow crystals. M.p 170°–171° C.

Elem. Anal. for: $C_{18}H_{21}N_2O_8P$: Calculated: C%=50.95, H%=4.99, N%=6.60. Found: C%=50.80, H%=4.97, N%=6.51.

IR$\nu_{max}^{KBr}$cm$^{-1}$: 3350, 3200, 1700, 1635, 1530, 1470, 1350, 1220, 1200, 1100, 1050.

NMR (CDCl$_3$) δ: 1.58~1.91 (1H, m), 2.32~2.58 (4H, m) [2.42 (3H, d, J=2.5 Hz)], 3.57H (3H, s), 3.83~4.66 (4H, m), 4.58 (1H, d, J=16 Hz), 4.86 (1H, d, J=16 Hz), 5.62 (1H, d, J=10 Hz), 7.22~7.33 (1H, m), 7.42~7.65 (3H, m).

EXAMPLE 8

Methyl 2-hydroxymethyl-6-methyl-5-(2-oxo-1,3,2-dioxaphosphorinan-2-yl)-4-(2-trifluoromethylphenyl)-1,4-dihydropyridine-3-carboxylate The 2-formyl compound (1.06 g) obtained in Example 5 was dissolved in 7 ml of methanol and, with ice cooling and stirring, 90 mg of sodium borohydrate was added thereto. After stirring for 1 hour, 20 ml of sodium chloride solution was added to the reaction solution, extracted with chloroform, the chloroform layer was washed with water, dried, concentrated, and the residue was purified by a flash chromatography to give 0.64 g of pale yellow powder.

Elem. Anal. for: $C_{19}H_{21}F_3NO_6P$: Calculated: C%=51.01, H%=4.73, N%=3.13. Found: C%=51.18, H%=4.92, N%=3.03.

IR $\nu_{max}^{KBr}$cm$^{-1}$: 3480, 3280, 1690, 1640, 1475, 1310, 1220, 1100, 1055, 1036.

NMR (CDCl$_3$) δ: 1.56~1.65 (1H, m), 1.65~1.76 (1H, m) 2.01~2.32 (1H, m), 2.35 (3H, d, J=2 Hz), 3.58 (3H, s), 3.82~4.60 (6H, m), 5.31~5.46 (1H, m), 7.18~7.64 (5H, m).

EXAMPLE 9

Methyl 5-diallyloxyphosphinyl-2-hydroxymethyl-6-methyl-4-(3-nitrophenyl)-1,4-dihydropyridine-3-carboxylate The 2-formyl compound (0.6 g) obtained in Example 6 was dissolved in 5 ml of methanol and, with ice cooling and stirring, 50 mg of sodium borohydrate was added thereto. The mixture was diluted with sodium chloride solution after 1 hour and extracted with chloroform. The extract was washed with water, dried, concentrated, and the residue was purified by a flash chromatography to give 0.55 g of pale yellow oil.

Elem. Anal. for: $C_{21}H_{25}N_2O_8P$: Calculated: C%=54.31, H%=5.43, N%=6.03. Found: C%=54.34, H%=5.44, N%=6.07.

IR $\nu_{max}^{film}$cm$^{-1}$: 3270, 3200, 3080, 1690, 1640, 1530, 1500, 1475, 1350, 1240, 1090, 1010.

NMR (CDCl$_3$) δ: 2.31 (3H,d,J=2 Hz), 2.4~3.1 (1H, br, D$_2$O disappeared, 3.64 (3H,s), 3.98~4.16 (1H, m), 4.21~4.46 (3H, m), 4.65~4.97 (3H, m), 4.98~5.34 (4H, m), 5.54~6.01 (2H, m), 7.32~7.69 (3H, m), 7.96~8.05 (1H, m), 8.06~8.16 (1H, m)

EXAMPLE 10

Methyl 2-cyano-6-methyl-4-(2-nitrophenyl)-5-(2-oxo-1,3,2-dioxaphosphorinan-2-yl)-1,4-dihydropyridine-3-carboxylate Methyl 2-formyl-6-methyl-4-(2-nitrophenyl)-5-(2-oxo-1,3,2-dioxaphosphorinan-2-yl)-1,4-dihydropyridine-3-carboxylate (1.8 g) was dissolved in 10 ml of methanol, then 354 mg of hydroxylamine hydrochloride and aqueous solution (2 ml) of 442 mg of sodium acetate were successively added with stirring at room temperature, and the mixture was stirred for 1.5 hours more. The reaction solution was concentrated at not higher than 30° C., the residue was dissolved in chloroform, the solution was washed with aqueous solution of sodium bicarbonate, washed with water, dried, and evaporated to give 1.84 g of crude oily oxime. The oxime (1.80 g) was dissolved in 25 ml of methylene chloride and the solution was heated to reflux for 2 days with 2.0 g of carbonyldiimidazole corresponding to three times as much amount. The reaction solution was washed with 5% hydrochloric acid, crystals separated out were collected by filtration, washed with water and then with methylene chloride, the filtrate was separated, the methylene chloride layer was washed with water, and evaporated. To the residue was added methylene chloride, crystals separated out were collected by filtration, combined with the crystals obtained previously, and recrystallized from ethyl acetate-methanol to give 0.92 g of pale yellow crystals, m.p. 228°–229° C.

Elem. Anal. for: $C_{18}H_{18}N_3O_7P$: Calculated: C=51.56, H=4.33, N=10.02. Found: C=51.18, H=4.55, N=10.03.

IR $\nu_{max}^{KBr}$ cm$^{-1}$: 3250, 3180, 3080, 2230, 1715, 1635, 1530, 1510, 1355, 1200, 1225, 1055.

NMR (CDCl$_3$) δ: 1.74~1.95 (1H, m), 2.13~2.32 (1H, m), 2.37 (3H, d, J=2.5 Hz), 3.65 (3H, s), 3.93~4.59 (4H, m), 5.67 (1H, d, J=10 Hz), 7.36~7.47 (1H, m), 7.50~7.68 (2H, m), 7.79 (1H, dd, J=1,8 Hz)

EXAMPLES 11

Methyl 2-cyano-6-methyl-5-(2-oxo-1,3,2-dioxaphosphorinan-2-yl)-4-(2-trifluoromethylphenyl)-1,4-dihydropyridine-3-carboxylate 2-Formyl compound (0.7 g) obtained in Example 5 was dissolved in 30 ml of methanol, 0.13 g of hydroxylamine hydrochloride and 0.16 g of sodium acetate were added thereto, and the mixture was dissolved in 30 ml of water to give a homogeneous solution. This was stirred at room temperature for 1.5 hours and concentrated in vacuo at below 30° C. Water was added to the residue, the mixture was neutralized with sodium bicarbonate, extracted with chloroform, and the extract was washed with water, dried and concentrated to give 0.76 g of the residue. The residue (0.57 g) and 0.4 g of carbonyldiimidazole were dissolved in 40 ml of methylene chloride, the mixture was heated to reflux for two days, washed with diluted hydrochloric acid and then with water, dried, and methylene chloride was evaporated therefrom. The residue was crystallized and recrystallized from ethyl acetate/n-hexane to give 0.38 g of yellow crystals, m.p 188.5°–189.5° C.

Elem. Anal. for: $C_{19}H_{18}F_3N_2O_5P$: calculated; c%=51.59, H%=4.10; N%=6.33. Found: C%=51.72, H%=4.32, N%=6.28.

I R $\nu_{max}^{KBr}$ cm$^{-1}$: 3400, 3260, 3200, 3080, 2220, 1715, 1635, 1510, 1310, 1230, 1110, 1050.

NMR (CDCl$_3$) δ: 1.70~2.30 (2H, m), 2.39 (3H, s), 3.73 (3H, s), 3.84~4.30 (2H, m), 4.36~4.72 (2H, m), 5.30~5.51 (1H, m), 7.05~7.65 (5H, m)

EXAMPLE 12

Methyl 2-cyano-5-diallyloxyphosphinyl-6-methyl-4-(3-nirophenyl)-1,4-dihydropyridine-3-carboxylate An aqueous solution (2 ml) containing 0.12 g of sodium acetate was added to 4 ml of methanolic solution of 0.1 g of hydroxylamine hydrochloride and 0.55 g of formyl compound obtained in Example 6 and the mixture was stirred at room temperature for 3 hours. To the reaction solution was added 10 ml of water, the mixture was neutralized with sodium bicarbonate, extracted with chloroform, and the extract was washed with water, dried, and concentrated to give 0.68 g of residue. To this was added 0.58 g of carbonyldiimidazole, the mixture was dissolved in 40 ml of methylene chloride, and the solution was heated to reflux for 2 days. The reaction solution was washed with diluted hydrochloric acid, washed with water, dried, concentrated and the residue was purified by flash chromatography to give 0.51 g of yellow oil.

Elem. Anal. for: $C_{21}H_{22}N_3O_7P$: Calculated: C%=54.90, H%=4.83, N%=9.15. Found: C%=54.69, H%=4.76, N%=9.09.

IR $\nu_{max}^{film}$ cm$^{-1}$: 3170, 3080, 2220, 1710, 1655, 1530, 1505, 1350, 1240, 1210, 1000, 980.

NMR (CDCl$_3$) δ: 2.35 (3H, d, J=2 Hz), 3.78 (3H, s), 4.08~4.25 (1H, m), 4.25~4.50 (3H, m), 4.93~5.26 (5H, m), 5.56~5.96 (2H, m), 7.38~7.52 (1H, m), 7.60~7.71 (2H, m), 8.02~8.07 (1H, m), 8.70~8.83 (1H, d, J=2 Hz).

Test Example.

Representative compounds (I) of the present invention were tested for their action in lowering blood pressure. The test procedure and results are as follows.

(1) The procedure where rats of normal blood pressure were used is as follows:

Blood pressure at the thigh artery of rats with normal blood pressure was measured, under unanesthetized condition, using a pressure transducer. The candidate compound was given per os at the dose of 1, 3 or 10 mg/kg, changes in blood pressure with time were measured, then the decreasing rate (%) of average artery blood pressure was calculated, and the blood pressure decreasing rate at the maximum depression was defined as "hypotensive action" given in table 1.

TABLE 1

| Compounds (Examples) | Hypotensive Action (%) | | |
|---|---|---|---|
| | 1 mg/kg | 3 mg/kg | 10 mg/kg |
| 7 | — | 19.4 | 32.8 |
| 8 | — | 17.7 | 38.3 |
| 9 | — | 12.4 | 14.2 |
| 10 | 39.9 | 48.9 | 44.9 |
| 11 | 24.0 | 38.0 | — |
| 12 | — | 2.6 | 16.7 |

(2) The procedure where spontaneous hypertensive rats (SHR) were used is as follows.

Male SHR's rats of more than 18 weeks age and not lower than 170 mmHg blood pressure at the contraction period were used (6 rats for one group). Measurement of blood pressure at the contraction period was conducted using a non-invasive blood pressure measuring apparatus. Rats were placed in a thermostat chamber kept at about 37° C. before the measurement and blood pressures were measured before and after (0.5, 1, 2, 3, 5 and 24 hours) administration of the candidate compounds. The dose showing 30% hypotensive action was defind as ED$_{30}$ and is given in Table 2. This experiment was conducted with rats that had been fasted from the previous day (about 16 hours).

TABLE 2

| Hypotensive Action (ED$_{30}$) in mg/kg (per os) | |
|---|---|
| Compound of Example 10 | 1.1 mg/kg |
| Compound of Example 11 | 1.6 mg/kg |

TABLE 2-continued

| Hypotensive Action (ED$_{30}$) in mg/kg (per os) | |
| --- | --- |
| Nifedipine | 1.5 mg/kg |

It will be apparent from Tables 1 and 2 that compounds (I) have a strong hypotensive and blood vessel dilating action due to their calcium antagonizing activity. Moreover their toxicity was very low, and, accordingly, the compounds (I) are calcium antagonists and have hypotensive and blood vessel dilating activity. As such, they are useful in the prophylaxis and treatment of circulatory diseases, such as hypertention, angina pectoris and cerebral circulation disorders.

What is claimed is:

1. A compound of formula (I):

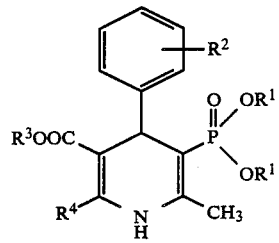

(I)

wherein $R^1$ is alkenyl of from two to six carbon atoms or alkyl of from one to about six carbon atoms or both of the depicted $R^1$ groups together represent trimethylene and form a six-membered ring together with the depicted oxygen and phosphorus atoms, $R^2$ is nitro, trifluoromethyl or halogen, $R^3$ is alkyl of from one to about six carbon atoms and $R^4$ is nitrile.

2. The compound according to claim 1, wherein $R^1$ is alkyl of from 1 to 4 carbon atoms.

3. The compound according to claim 1, wherein $R^2$ is nitro, trifluoromethyl, chlorine, bromine, fluorine or iodine.

4. The compound according to claim 1, wherein $R^2$ is in the 2- or 3-position of the depicted phenyl ring.

5. The compound according to claim 1, wherein $R^3$ is alkyl of from 1 to 4 carbon atoms.

6. The compound according to claim 1, which is methyl 2-cyano-6-methyl-4-(2-nitrophenyl)-5-(2-oxo-1,3,2-dioxaphosphorinan-2-yl)-1,4-dihydropyridine-3-carboxylate.

7. The compound according to claim 1, which is methyl 2-cyano-6-methyl-5-(2-oxo-1,3,2-dioxaphosphorinan-2-yl-)-4-(2-trifluoromethylphenyl)-1,4-dihydropyridine-3-carboxylate.

8. The compound according to claim 1, which is methyl 5-diallyloxyphosphinyl-2-hydroxymethyl-6-methyl-4-(3-methyl 2-cyano-6-methyl-4-(2-nitrophenyl)-5-(2-oxo-1,3,2-dioxaphosphorinan-2-yl)-1,4-dihydropyridine-3-carboxylate; methyl 2-cyano-6-methyl-5-(2-oxo-1,3,2-dioxaphosphorinan-2-yl)-4-(2-trifluoromethylphenyl)-1,4-dihydropyridine-3-carboxylate, or methyl 2-cyano-5-diallyloxyphosphinyl-6-methyl-4-(3-nitrophenyl)-1,4-dihydropyridine-3-carboxylate.

9. A pharmaceutical composition for the prophylaxis or treatment of hypertension, angina pectoris or cerebral circulation disorders in animals, including humans, which comprises an effective amount of a compound according to claim 1 in combination with a pharmaceutically acceptable diluent or carrier.

10. A method for the prophylaxis or treatment of hypertension, angina pectoris or cerebral circulation disorders in animals, including humans, which comprises administering to an animal, including humans, in need thereof an effective amount of a compound according to claim 1.

* * * * *